(12) United States Patent
Tuma et al.

(10) Patent No.: US 7,688,998 B2
(45) Date of Patent: Mar. 30, 2010

(54) ADJUSTABLE MARKER ARRANGEMENT

(75) Inventors: Gregor Tuma, Munich (DE); Norman Plassky, Erfurt (DE)

(73) Assignee: BrainLAB AG, Feldkirchen (DE)

( * ) Notice: Subject to any disclaimer, the term of this patent is extended or adjusted under 35 U.S.C. 154(b) by 1449 days.

(21) Appl. No.: 11/057,081

(22) Filed: Feb. 11, 2005

(65) Prior Publication Data

US 2005/0267358 A1    Dec. 1, 2005

Related U.S. Application Data

(60) Provisional application No. 60/548,153, filed on Feb. 25, 2004.

(30) Foreign Application Priority Data

Feb. 11, 2004   (EP)   ................................. 04003019

(51) Int. Cl.
*G06K 9/00* (2006.01)
(52) U.S. Cl. ....................... 382/103; 382/128
(58) Field of Classification Search ................ 382/103, 382/128, 132, 133, 287; 700/259; 348/135; 600/424, 426
See application file for complete search history.

(56) References Cited

U.S. PATENT DOCUMENTS

| | | | |
|---|---|---|---|
| 6,190,395 B1 | 2/2001 | Williams | 606/130 |
| 6,226,548 B1 | 5/2001 | Foley et al. | 600/426 |
| 6,973,202 B2 * | 12/2005 | Mostafavi | 382/103 |
| 7,529,387 B2 * | 5/2009 | Kotake et al. | 382/103 |
| 2003/0210812 A1 * | 11/2003 | Khamene et al. | 382/128 |
| 2003/0225329 A1 | 12/2003 | Rossner et al. | 600/424 |

FOREIGN PATENT DOCUMENTS

| | | |
|---|---|---|
| DE | 201 03 416 U1 | 8/2001 |
| DE | 203 03 499 U1 | 6/2003 |
| DE | 203 03 643 U1 | 8/2003 |
| WO | WO02/064042 A1 | 8/2002 |
| WO | WO2004/030558 A1 | 4/2004 |

OTHER PUBLICATIONS

Notification from the EPO dated Dec. 28, 2007 together with the Opposition, grounds for Opposition and cited references.

(Continued)

*Primary Examiner*—Andrew W Johns
(74) *Attorney, Agent, or Firm*—Renner, Otto, Boisselle & Sklar, LLP

(57) ABSTRACT

The invention relates to a reference star adapter and a method of re-calibrating a previously registered body using the reference star adapter. The reference star adapter includes a first fixing element for coupling the reference star adapter to a body, and a second fixing element for coupling the reference star adapter to a plurality of markers. At least one joint is coupled between the first fixing element and the second fixing element, and at least one position detector is operatively coupled to the at least one joint, wherein the at least one position detector provides data describing a position or a geometry of the at least one joint.

12 Claims, 7 Drawing Sheets

OTHER PUBLICATIONS

Notification from the EPO dated Jan. 25, 2008 with enclosures A4, E6 and E8.
Notification from the EPO dated Apr. 29, 2009 together with a letter from the Opponent dated Mar. 23, 2009 and additional documents introduced into the proceedings.
Aesculap reference, Anlage 5.
Langlotz et al., "Computer Assisted Orthopaedic Surgery", 3rd Annual Meeting of CAOS-International-Proceedins, Jun. 2003, Brisson et al., "Precision freehand sculpting of bone," pp. 36-37.
Computer Aided Surgery, vol. 8, No. 5, 2003, CURAC Special Issue, pp. 247-256, Korb et al., "Development and First Trial of a Surgical Robot for Complex Trajectory Milling".
Prof. Dr.-Ing. Heniz Worn, Ausdruck PowerPoint-Vortag, "Neue Methoden der rechner- und robotikgestützten Kopfchirurgie", 2. Jahrestagung der Deutschen Gesellschaft für Computer-und Roboterassistierte Chirurgie, (CURAC) Nov. 2003.
Korb et al., "Risk analysis for a reliable and safe surgical robot system", International Congress Series 1256 (2003), pp. 766-770.

* cited by examiner

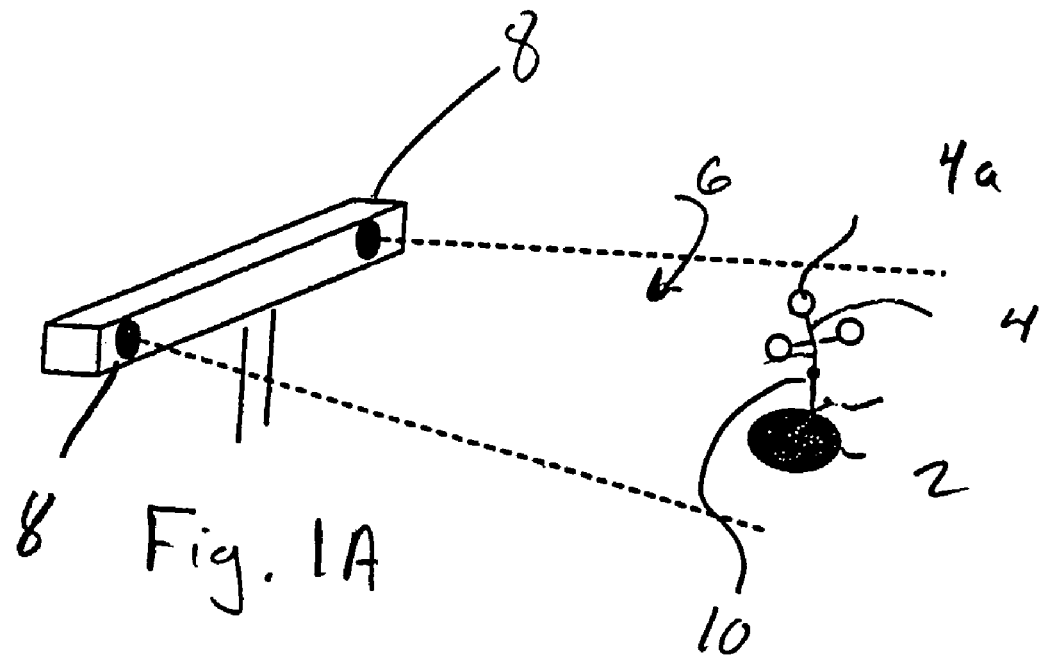
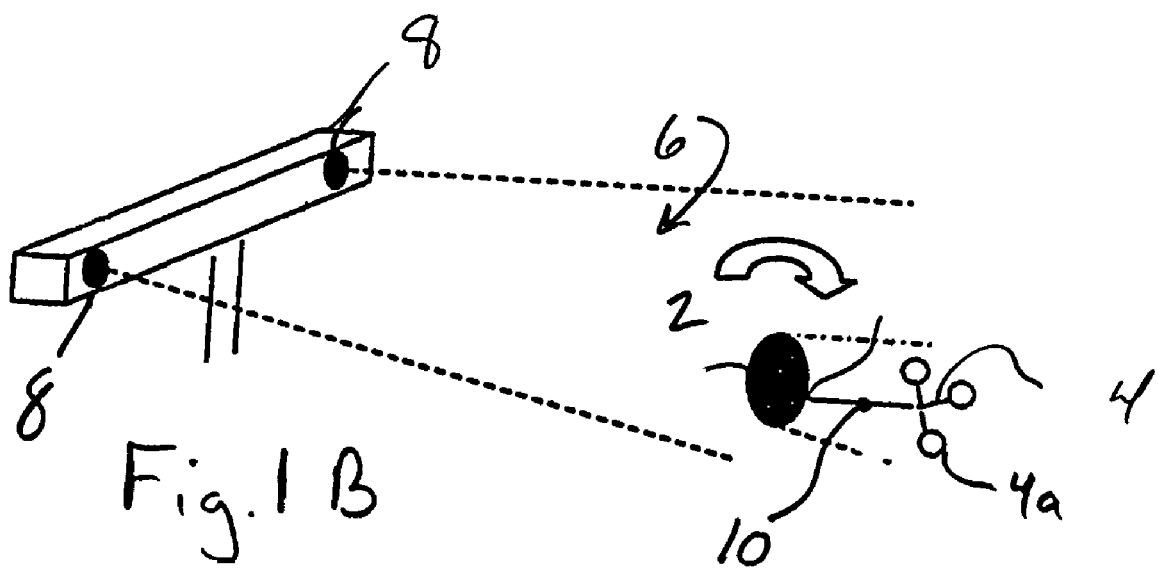

ADJUSTABLE MARKER ARRANGEMENT

RELATED APPLICATION DATA

This application claims priority of U.S. Provisional Application No. 60/548,153 filed on Feb. 25, 2004, which is incorporated herein by reference in its entirety.

FIELD OF THE INVENTION

The present invention relates to an adjustable marker arrangement and, more particularly, to a marker system that can be used with a medical navigation system. The marker system includes an adapter having at least two ends, wherein a first end is attached to a body or an instrument, and a second end is attached to a reference marker, such as a reference star. The marker system allows the medical navigation system to ascertain the position of the adapter and, therefore, the position of the body or instrument, in three dimensional space.

BACKGROUND OF THE INVENTION

Medical navigation systems, such as image-assisted systems, provide navigational information to a surgeon via a display, for example. The navigational information can be in the form of images and/or text, and can be used by the surgeon to determine the relative location of a particular bone, joint, tumor, etc. of a patient with respect to one or more preoperative images of the patient.

Prior to providing the navigational information, the patient and, more particularly, the area of interest of the patient, is registered. Registration is the process of instructing or teaching the medical navigation system the position of the area of interest in three dimensional space. Once registered, the navigation system correlates the area of interest with the preoperative images of the patient. Moreover, the navigation system tracks the area of interest and provides visual, numerical and/or textual information with respect to the preoperative images on the display. Additionally, the navigation system can display the position of surgical instruments utilized on the patient with respect to the preoperative images in real time.

Navigation systems use a computer connected to one or more tracking sensors or cameras, such that the position of markers fixed to the patient and/or to the instruments can be ascertained, from which the position of the patient and/or instruments can be determined. Such markers, which can include both active emitters and passive reflective markers, can be attached via adapters to a patient and/or to surgical instruments (e.g., a scalpel, forceps, a microscope, a pointer, etc.).

Often, an adapter is used that includes a first fixing element and a second fixing element. The first fixing element, which can be a clamp, is used to attach the adapter to the patient or instrument. The second fixing element is used to attach a reference star. Reference stars are well known in the art and generally include three or four arms extending outwards with active or passive markers attached to the outer ends of the arms. A known navigation system that uses the reference star described above is the image-assisted navigation system VectorVision™, available from BrainLAB AG, and described, for example, in US Patent Publication No. 2003/0225329, which is hereby incorporated by reference.

During surgery, a number of reference stars having different geometries can be arranged within a surgeon's limited working area. The different geometries permit the navigation system to distinguish between each reference star and, therefore, between each instrument or body part attached to the particular reference star. Using a number of reference stars, however, can lead to overlap between reference stars within the cameras' field of vision and/or to individual markers or entire reference stars being obscured from the cameras' field of vision. For example, and with reference to FIGS. 1A and 1B, when the body 2 or an extremity of the patient is moved, the movement can lead to the reference star 4 or a portion thereof exiting the field of vision 6 of the cameras 8. If, in order to re-position the reference star 4 within the field of vision 6, the reference star adapter 10 were detached from the body 2 and then reattached such that the reference star 4 were within the field of vision 6, then the patient would have to be re-registered.

FIG. 2 illustrates a flow diagram 20 of prior art steps performed when the reference star moves out of the cameras' field of vision. Beginning at block 22, a reference star adapter 10 is used to rigidly couple a reference star 4 to a body 2, e.g., an instrument or a region of a patient, and placed in an initial position such that the markers 4a of the reference star 4 are within the field of vision 6 of the cameras 8. At block 24, the body is registered in the navigation system using conventional techniques. Registration of a body in a navigation system generally includes identifying numerous points on the body in three dimensional space to the navigation system. Once sufficient points have been identified, the navigation system correlates the data to preoperative images of the patient.

Once registered, the reference star 4 is tracked by the navigation system, as indicated at block 26. Moreover, since the reference star 4 is rigidly coupled to the body 2, the body also is tracked by the navigation system. Should the reference star 4 become obscured from the field of vision 6 of the cameras 8 as indicated at block 28, then the reference star 4 and the body 2 can no longer be tracked by the navigation system. This can occur, for example, when the body 2 is rotated such that all or part of the markers 4a of the reference star 4 are obscured from the field of vision 6 of the cameras 8. Sometimes, this can be corrected by repositioning the cameras 8 of the navigation system, thereby returning the reference star 4 into their field of vision 6, as indicated at block 30. If this does not correct the problem, then at block 32 the reference star 4 is repositioned by decoupling the reference star adapter 10 from the body 2 and re-coupling it such that the reference star 4 again is within the field of vision 6 of the cameras 8. However, since the reference star adapter 10 is decoupled from the body 2, the navigation system loses the position of the body and, consequently, the body 2 must be re-registered as indicated at block 34. Once re-registered, tracking of the reference star 4 and the body 2 can continue, as indicated at block 36.

SUMMARY OF THE INVENTION

The present invention provides an apparatus and method that facilitates adjusting the position of a reference star without the need to re-register the body to the navigation system.

According to one aspect of the invention, a reference star adapter comprises a first fixing element for coupling the reference star adapter to a body; a second fixing element for coupling the reference star adapter to a plurality of markers; at least one joint coupled between the first fixing element and the second fixing element; and at least one position detector operatively coupled to the at least one joint, wherein the at least one position detector provides data describing a position or a geometry of the at least one joint.

According to another aspect of the invention, a method of re-calibrating a previously registered body in a navigation system wherein the body is coupled via at least one joint to a plurality of reference markers that are detectable by the navigation system, the navigation system has a specified field of vision in which the markers are detectable, and the navigation system stores position data of the registered body, comprises the steps of: re-positioning the plurality of reference markers with respect to the body such that the plurality of reference markers are within the field of vision of the navigation system; and detecting a change in position of the reference markers with respect to the body.

According to yet another aspect of the invention, a program embodied in a computer-readable medium for re-calibrating a previously registered body in a navigation system, the body being coupled via at least one joint to a plurality of reference markers that are detectable by the navigation system, the navigation system having a specified field of vision in which the markers are detectable, and the navigation system storing position data of the registered body, comprises: code that provides an indication that the plurality of reference markers are not within the field of vision of the navigation system; and code that detects a change in position of the reference markers with respect to the body.

According to a further aspect of the invention, a system for re-calibrating a previously registered body in a navigation system, the body being coupled via at least one joint to a plurality of reference markers that are detectable by the navigation system, and the navigation system having a specified field of vision in which the markers are detectable, and the navigation system storing position data of the registered body, comprises: a processor circuit having a processor and a memory; a calibrating system stored in the memory and executable by the processor, the calibrating system including: logic that generates an indication that the plurality of reference markers are not within the field of vision of the navigation system; and logic that detects a change in position of the reference markers with respect to the body.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

The foregoing and further features of the present invention will be apparent with reference to the following description and drawings, wherein:

FIGS. 1A to 1B illustrate a body connected to a reference star adapter in accordance with the prior art;

DETAILED DESCRIPTION

Figure 2:
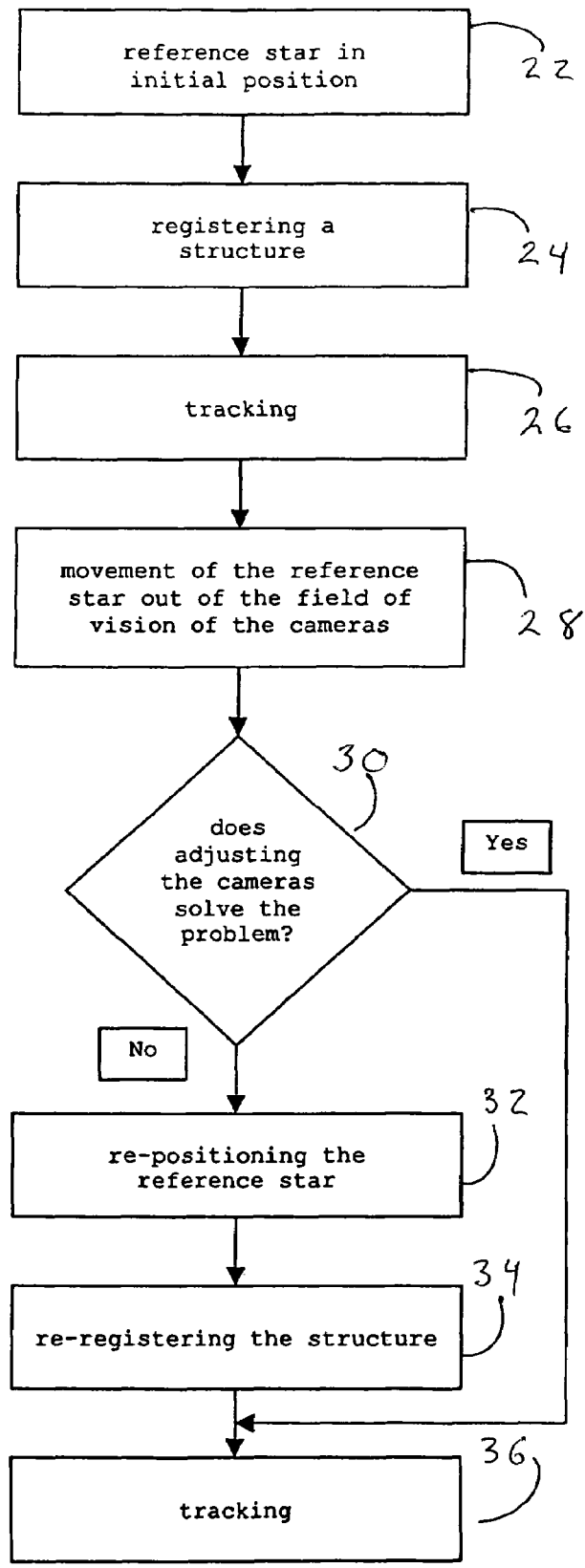
FIG. 2 is a flow diagram for re-registering a patient in accordance with the prior art.
Figure 3A:
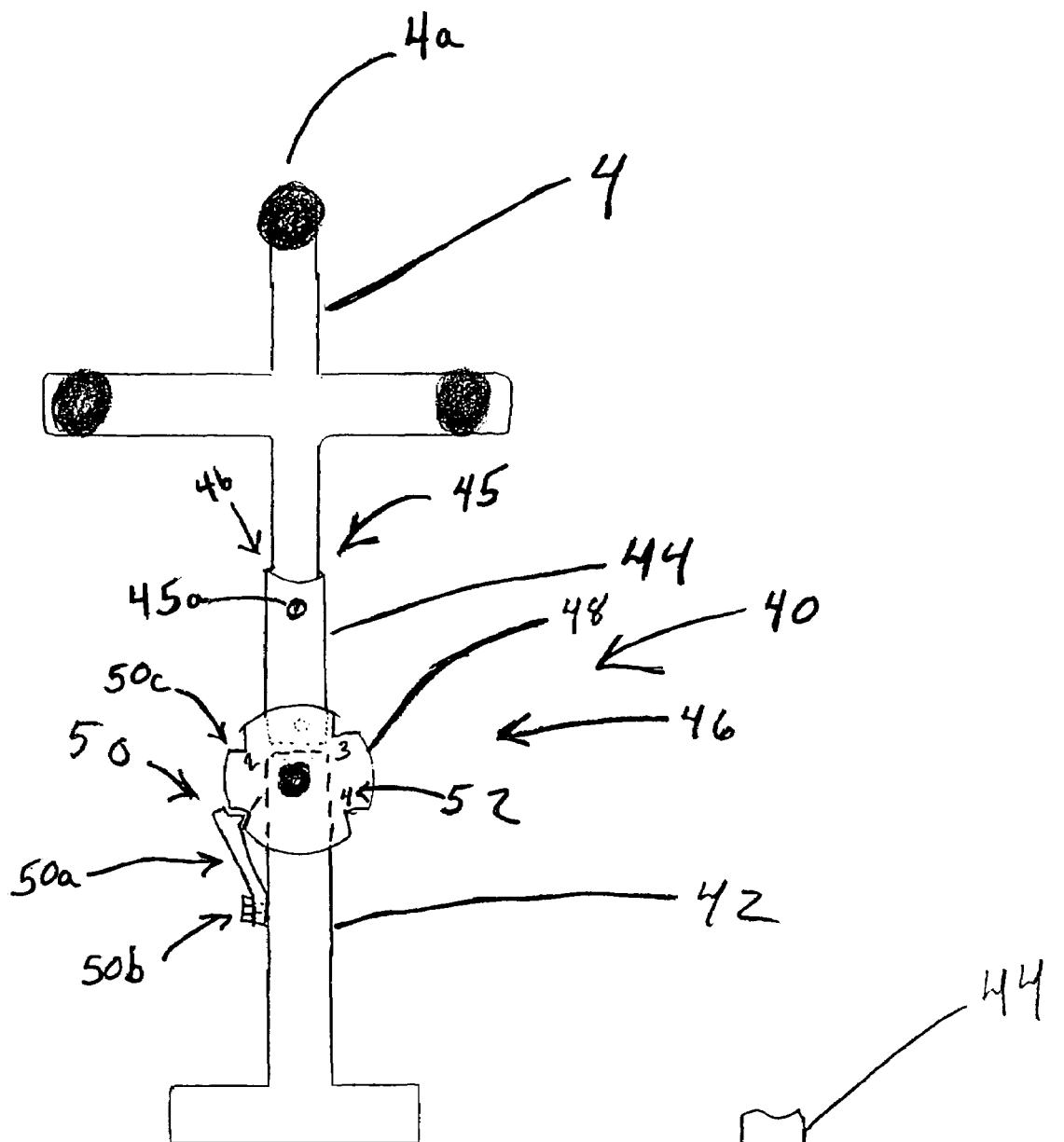
FIG. 3A illustrates a front view of a reference star adapter coupled to a reference star in accordance with an embodiment of the present invention.
Figure 3B:
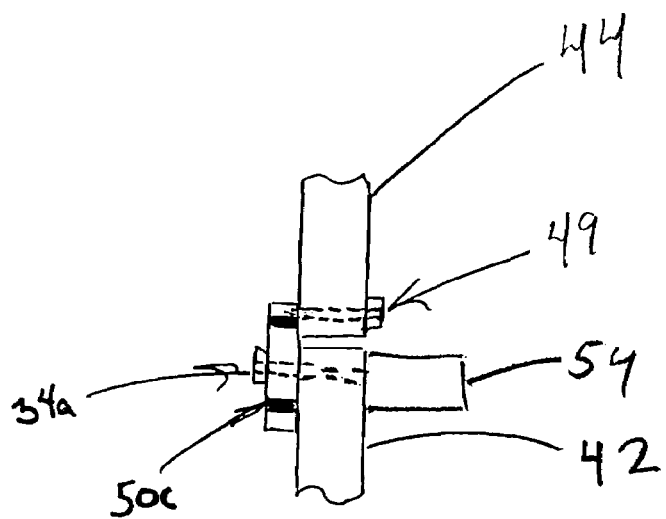
FIG. 3B illustrates a side view of the reference star adapter of FIG. 3A.

The present invention provides a reference star adapter and a method for re-calibrating an instrument or body using the reference star adapter, which can increase the speed and efficiency of image-assisted medical navigation systems. FIG. 3A illustrates a front view of a reference star adapter 40 in accordance with an embodiment of the invention, wherein a reference star 4 is coupled to the adapter 40. FIG. 3B illustrates a side view of a portion of the adapter 40, without the reference star.

The illustrated exemplary reference star adapter 40 includes a first fixing element 42, such as, for example, a clamp for attaching the adapter 40 to an instrument. Alternatively, the first fixing element can include a base having one or more screw holes (not shown), wherein screws, nails or the like are used to attach the first fixing element to a body, e.g., a bone. A second fixing element 44 includes a socket 45, wherein a reference star 4 can be coupled to the second fixing element via the socket. A clamping means 45a, such as a hold down screw, can provide a clamping force between the reference star and a wall of the socket, thereby securing the reference star to the second fixing element. Alternatively, the socket 45 and one end 4b of the reference star 4 can be threaded, such that the reference star can be screwed into the socket 45, thereby securing the reference star to the second fixing element. In accordance with the invention, at least one bearing or joint 46 is provided between the first fixing element 42 and the second fixing element 44. The bearing or joint 46 enables the second fixing element to be geometrically adjusted relative to the first fixing element.

As used herein, a bearing or a joint refers to a connection between two or more members, wherein a geometric relationship between the two or more members can be altered while the two or more members remain physically connected to one another. For example, a pivoting joint between a first and second member allows an angular relationship between the two members to be altered. A sliding bearing, on the other hand, allows the length of at least on member to be altered.

The at least one bearing provided between the first fixing element 42 and the second fixing element 44 can be a movable bearing, such as, for example, a transverse bearing, a sliding bearing or a rolling bearing. Alternatively, the at least one bearing can be a fixed bearing, such as, for example, a transverse and longitudinal bearing or a fixed joint. The joint can be formed as a turning joint, sliding joint, cam joint, screw joint, turning and sliding joint, ball joint or plate joint. Additionally, a combination of different bearings or joints can be used to enable a reference star 4 fixed to the second fixing element 44 to be moved in all six degrees of freedom with respect to the first fixing element 42. For sake of simplicity, the term "joint" will used throughout the remainder of the disclosure to describe the present invention, and shall be construed to include at least one bearing and/or at least one joint as described above.

An active or passive position detector 48, which provides data describing or defining the position or geometry of the at least one joint 46, is connected to the joint. The position detector 48 can provide analog and/or digital position information to a controller, such as a computer controller. Alternatively, the position detector 48 may provide visual feedback of the current position of the joint 46, which then may be manually entered into the computer controller. The second fixing element 44 can be coupled to the position detector 48 and/or the joint 46 via a fastening means 49, such as a screw, rivit, bolt or the like.

Preferably, at least one position detector 48 is provided for each joint 46 in the system. By using a position detector it is possible to automatically or manually re-position the second fixing element 44 with respect to the first fixing element 42, thereby repositioning the reference star 4 (which is connected to the second fixing element) with respect to the body 2. As used herein, a body refers to an object, such as an instrument or a portion of a patient's body, e.g., a particular bone, that can be attached to the first fixing element.

For example, the second fixing element 44 can be rotated and/or shifted along one or more predetermined directions, wherein the at least one position detector 48 can ascertain what movement the second fixing element has performed with respect to its previous position. Thus, re-registering is unnecessary, since the new positional relationship between the second fixing element 44 and the first fixing element 42 can be determined.

For example, a computer program executed by a processor can monitor the position feedback signal from the at least one position detector 48. Based on the position feedback signal, the processor can calculate the change in position of the second fixing element 44 with respect to the first fixing element 42. Since the reference star 4 is coupled to the second fixing element and the body 2 is coupled to the first fixing element, the change in position of the reference star 4 with respect to the body 2 also can be calculated. Thus, the reference star 4 is once again in a defined positional relationship to the body 2, provided the body has been registered beforehand. Consequently, re-registering is not necessary after a change in position of the reference star with respect to the body, thus facilitating repositioning of one or more reference stars during surgery.

The joint 46 of the reference star adapter 40 may be configured such that the joint can only be fixed or arrested at defined predetermined positions. For example, a tooth or a latch mechanism 50 is provided on the joint 46 or as part of the position determining element 48. The mechanism 50 enables the joint to be moved continuously but is stable only at predetermined latching positions. The latch mechanism 50 can include a latch 50*a*, which is coupled to the first fixing element 42 via a fastening means 50*b*, e.g., a screw, rivit, etc. Notches 50*c* releasably engage with the latch 50*a*, thereby retaining the joint 48 in a known position.

Preferably, markings 52 are provided at the predetermined latching positions of the joint 46 and/or the position determining element 48, wherein the markings are used as position indicators. For example, a user of the reference star adapter 40 in accordance with the invention can read from the marking the position the joint currently is situated. If a continuously adjustable joint is used, then it also is possible to provide a display, which in the case of a turning joint, displays the aperture angle of the joint such that once the joint has been arrested, a user can read the current position of the joint 46 and/or the relative change in position of the joint. It is equally possible to provide position detectors 48 on one or more joints, wherein the position detectors measure or ascertain the movement of the joint. Angular or linear sensors, for example, can be used as position detectors 48 that qualitatively ascertain a rotation, such as an aperture angle of a joint, or a translation, such as the shift of a mounted axis. The ascertained positional values (e.g., the rotation, aperture angle and/or the translation) can be displayed by the navigation system. The positional values can be manually entered (e.g., typed into the navigation system) or automatically entered into the navigation system. For example, the individual position sensors can be connected to the navigation system by cable, radio (e.g., Bluetooth), or an infrared interface, in order to convey the position or change in position of the second fixing element 44 with respect to the first fixing element 42 to the navigation system.

Furthermore, the reference star adapter 40 may be semi-automatic or automatic. For example, one or more actuators 54, such as a motor coupled to the joint 46 via a shaft 54*a*, can be provided to drive the position of the second fixing element 44 and, thus, drive the position of the reference star 4. A position detector 48 can be provided on the actuator or, alternatively, the actuator can be a precision controlled system, e.g., a servo motor and controller, such that the change in the position of the reference star 4 caused by the actuator 54 is exactly defined and can be transmitted to the navigation system.

As will be appreciated, a navigation system can include at least one reference star adapter 40 as described above and a reference star 4. The navigation system, which may further include at least two cameras 8 and a computational unit, ascertains the position in three-dimensional space of the reference star 4 and, therefore, the position in three-dimensional space of the first and second fixing elements 42, 44. For example, infrared light is emitted towards the reference star 4 and, as the infra-red light strikes the reflective markers 4*a* of the reference star 4, a portion of the infra-red light is reflected back towards the cameras 8. Each camera provides two-dimensional data relating to the reference star to the computational unit. The computational unit, using the two-dimensional data from the cameras 8, calculates the position in three-dimensional space of the reference star 4 using conventional techniques. Alternatively, the cameras 8 can calculate the position in three-dimensional space and provide the position to the computational unit.

Figure 4A:
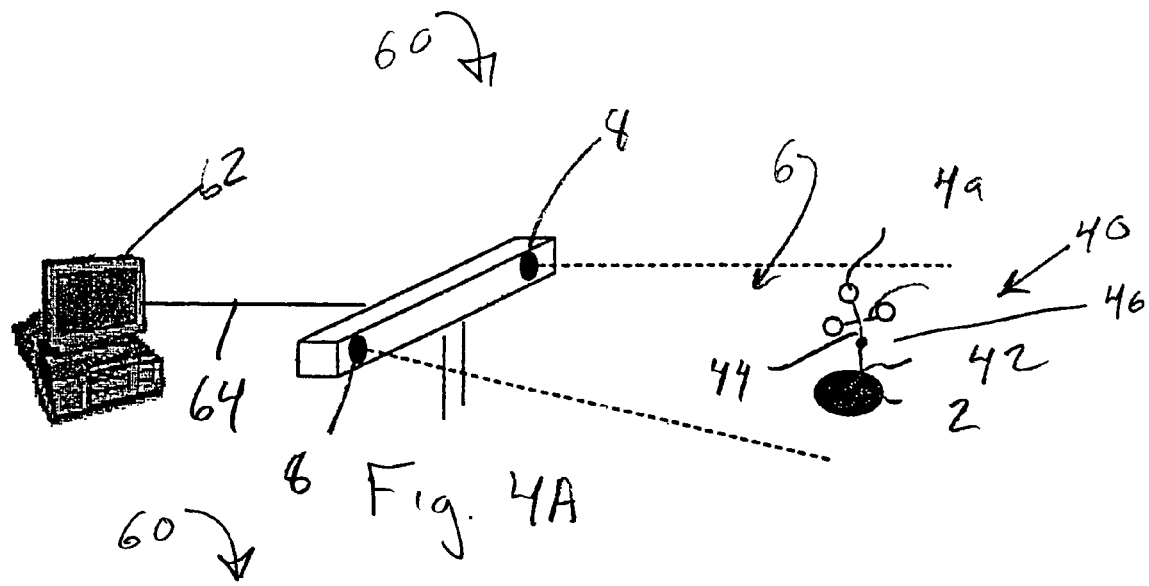
FIGS. 4A-4C illustrate a system for re-calibrating a reference star in accordance with an embodiment of the present invention.
Figure 4B:
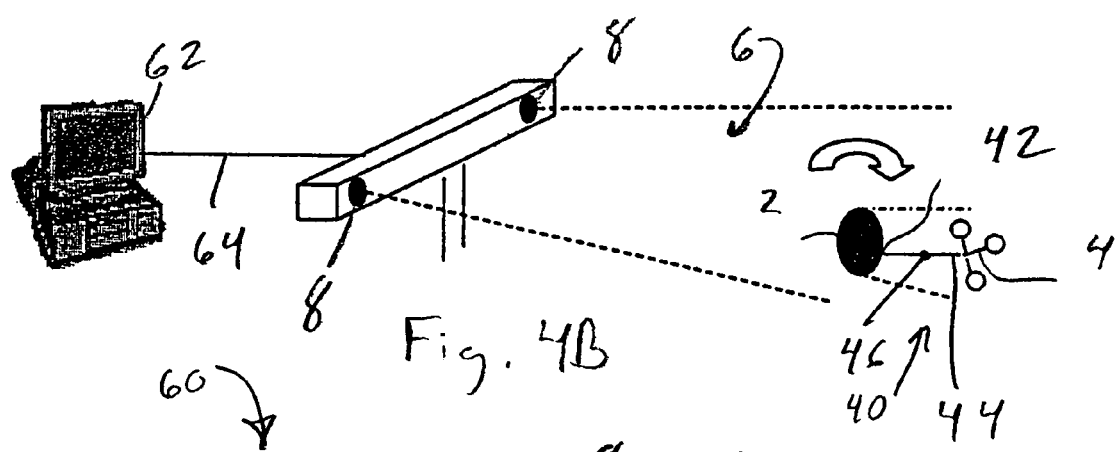
Figure 4C:
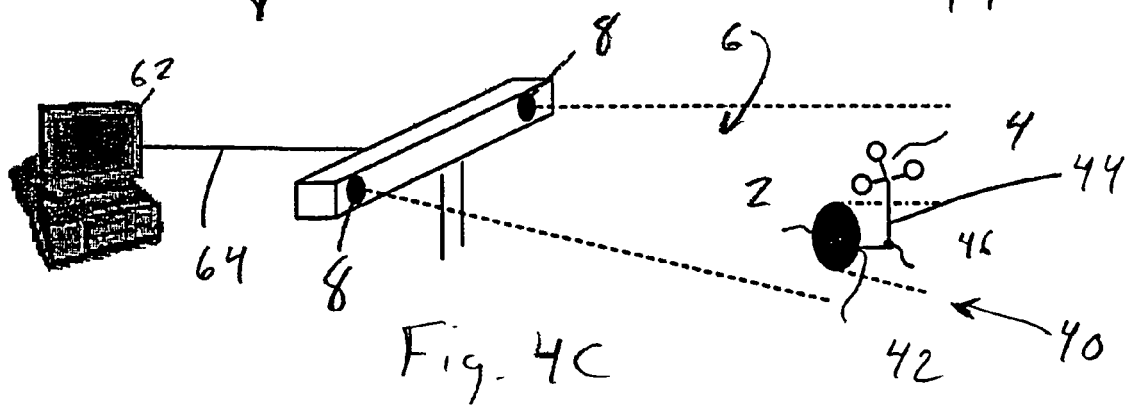

With reference to FIGS. 4A-4C, a navigation system 60 utilizing an adapter 40 in accordance with the above described embodiment is illustrated. The navigation system 60 includes cameras 8, which, for example, can be conventional infrared light detecting cameras used in three-dimensional position detecting applications. Additionally, the navigation system includes a computational unit 62, which, for example, can be a computer based system capable of executing program code. In one embodiment, the computational unit 62 is a PC based desktop computer system. The computational unit 62 can be coupled to the cameras 8 via a communications link 64, such as a wired or wireless communications link.

As infrared light is directed towards and strikes the passive markers 4*a* of the reference star 4, the cameras 8 detect the passive markers that are within the field of vision 6 of the cameras, while markers that are not within the field of vision 6 are not detected. The passive markers 4*a* are affixed to a reference star 4, which in turn is affixed to a body 2 via the adapter 40 of the present invention. The adapter 40 includes a joint 46, which couples a first fixing element 42 to a second fixing element 44. The first fixing element 42 is coupled to the body 2, while the second fixing element 44 is coupled to the reference star 4.

In the following description, it is assumed that the body 2 previously has been registered with the navigation system using conventional techniques. During operation of the navigation system, the position of the markers 4*a* detected by the cameras 8 is forwarded to the computational unit 62, and the computational unit calculates the position of the reference star 4 in three-dimensional space using conventional techniques.

If the body 2 were rotated as shown in FIG. 4B, such that the reference star 4 is obscured by the body 2, then the cameras 8 could no longer detect the markers 4a and, therefore, the navigation system could not calculate the position of the reference star 4.

Using the reference star adapter 40 of the present invention, the reference star 4 can remain connected to the body 2 and, via the joint 46, be shifted, rotated and/or tilted, such that the reference star again is within the field of vision 6 of the cameras 8, as shown in FIG. 4C. Movement of the joint 46 can be performed manually, e.g., by hand, or automatically, e.g., by a motor.

Moreover, re-registering of the body is not required, since, in accordance with the invention, a position sensor or decoder 48 is provided on the joint 46 that can detect the quantitative movement of the joint 46. Data relating to the quantitative movement is conveyed (either automatically or manually) to the computational unit 62 of the navigation system 60, thus permitting the computational unit to calculate the change in position of the second fixing element (and thus the reference star) with respect to its original registered position. Knowing the change in position of the second fixing element 44, the navigation system 62 can automatically re-calibrate the second fixing element by calculating the new positional relationship between the second fixing element and the first fixing element 42. Moreover, since the reference star 4 is coupled to the second fixing element 44, and the body 2 is coupled to the first fixing element 42, the reference star 4 also can be re-calibrated with respect to the body 2, provided the geometry or structure of the adapter 40 or the joint 46 is known.

The change in the position of the reference star can be automatically transmitted to the navigation system, such that the position is continuously re-calibrated while the reference star 4 is moved relative to the body 2. Alternatively, the change in position of the reference star can be re-calibrated after the change in position is completed. For example, the computational unit 62 may re-calibrate the change in position after the joint has not been moved for a pre-set time period.

It should be appreciated that while the functional principle of the invention shown in FIGS. 4A-4C has been described on the basis of a reference star 4 connected to a body 2, it is equally possible for the reference star 4 to be connected to an instrument, e.g., a surgical instrument. Additionally, the number of joints can be increased to meet the requirements of the application.

Figure 5A:
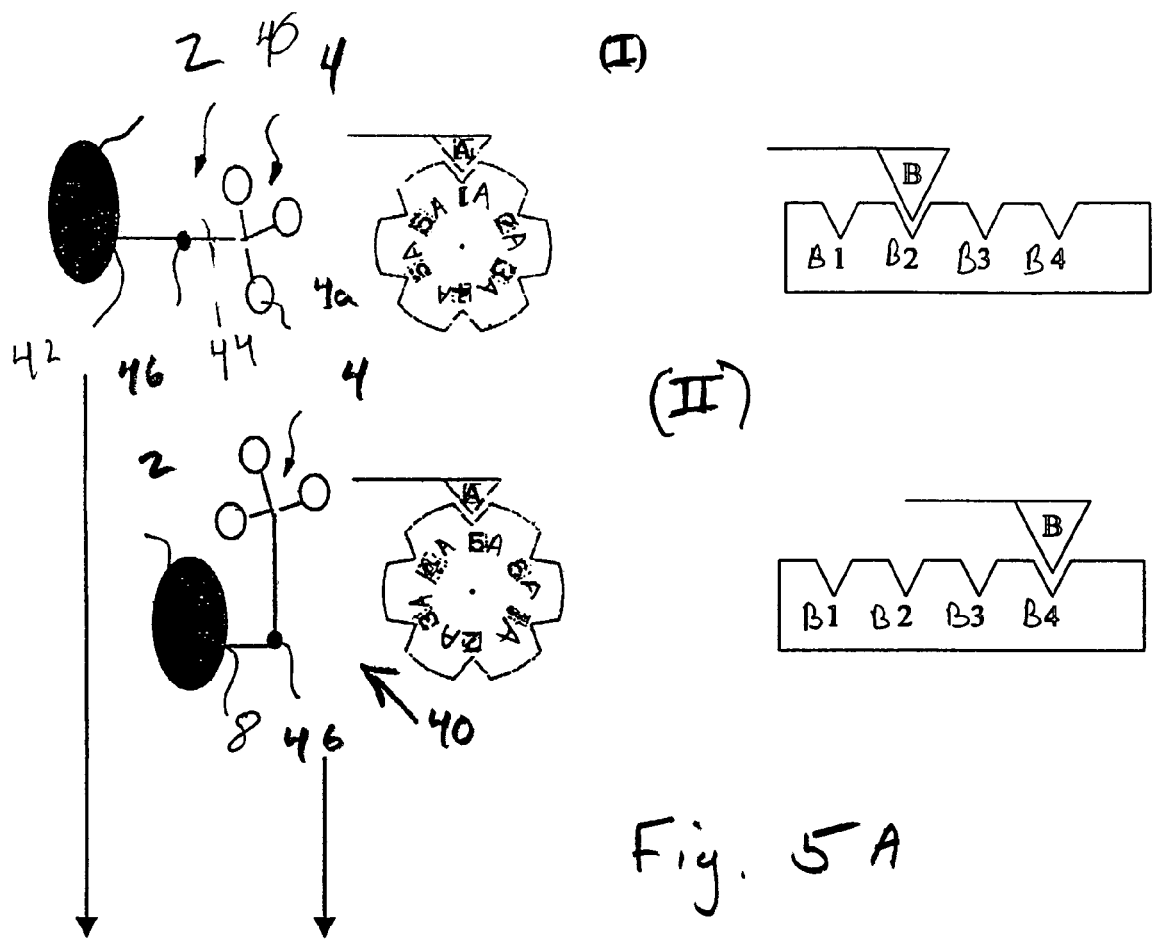
FIGS. 5A-5B illustrate an adjusting mechanism in accordance an embodiment of the present invention.
Figure 5B:
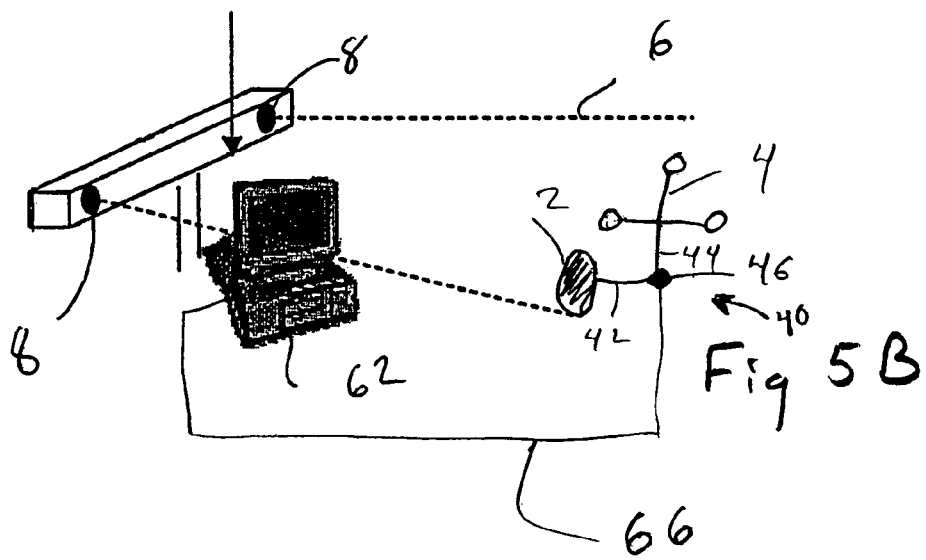

Moving now to FIGS. 5A and 5B, an exemplary embodiment of an adjusting mechanism of the reference star adapter 40 in accordance with the present invention is shown. Two positions of the reference star adapter are shown; an initial position (I) and a second position (II). A reference star 4 is connected to a body 2 by means of the reference star adapter 40, which includes an adjusting mechanism 46 having a turning joint A and a sliding bearing B. In the exemplary embodiment, the turning joint A can be latched in six different turning positions (positions A1 to A6). The sliding bearing B can be latched in four different positions (positions B1 to B4). It should be appreciated that the number of latching positions for the turning joint A and the sliding bearing B are merely exemplary and more or fewer latching positions can be implemented without departing from the scope of the invention.

In the initial position (I), the position code for the position sensor is A1B2, signifying that the turning joint A is in position A1 and the sliding bearing B is in position B2. If the body 2 is moved such that the reference star 4 is no longer in the field of vision 6 of the cameras 8 (e.g, the body 2 obscures the reference star 4), then the reference star, via the joint 46, can be moved to a position in which it is no longer obscured. As was noted above, movement of the joint 46 can be performed manually or automatically. The movement can be angular, e.g., changing the angular relationship between the first fixing element 42 and the second fixing element 44 via the turning joint A, or linear, e.g., changing the length of the second fixing element 44 via the sliding bearing B.

Once the position of the reference star 4 has been adjusted, the turning joint A is latched in the turning position, e.g., position A5 shown in the second position (II) of FIG. 5A, and the sliding bearing B is latched, e.g., position B4 shown in the second position (II) of FIG. 5A.

In the second position (II), the position code for the position sensor is A5B4, signifying that the turning joint A is in position A5 and the sliding bearing B is in position B4. This code can be communicated to the computational unit 62 automatically via a communications link 66, e.g., via a wireless CR wired communication link, or manually, e.g., a user typing the code into the computational unit 62. If the geometry of the reference star adapter 40 and the adjustment options of the bearings and joints are known to the navigation system 60 (preferably, the geometry or structure of the adapter and/or of the at least one joint or bearing is stored in a database of the computational unit 62), then the new positional relationship between the adjusted reference star 4 and the body 2 can be calculated. Consequently, the elaborate registering methods following a re-positioning of the reference star 4, known from the prior art, can be omitted.

For example, if the six latch points of the turning joint A were separated by 60 degree increments, and the four latch points of the sliding bearing B were separated by one inch increments, then, based on the position code received by the computational unit 62 (either automatically or manually), the computational unit 62 could calculate new registration coordinates based on the new position of the second fixing element and the known geometry of the reference star adapter 40.

Accordingly, the reference star adapter 40 permits a reference star that is coupled to a body and previously registered in a navigation system, to be moved with respect to the body without requiring the body or instrument to be re-registered in the navigation system.

Figure 6:
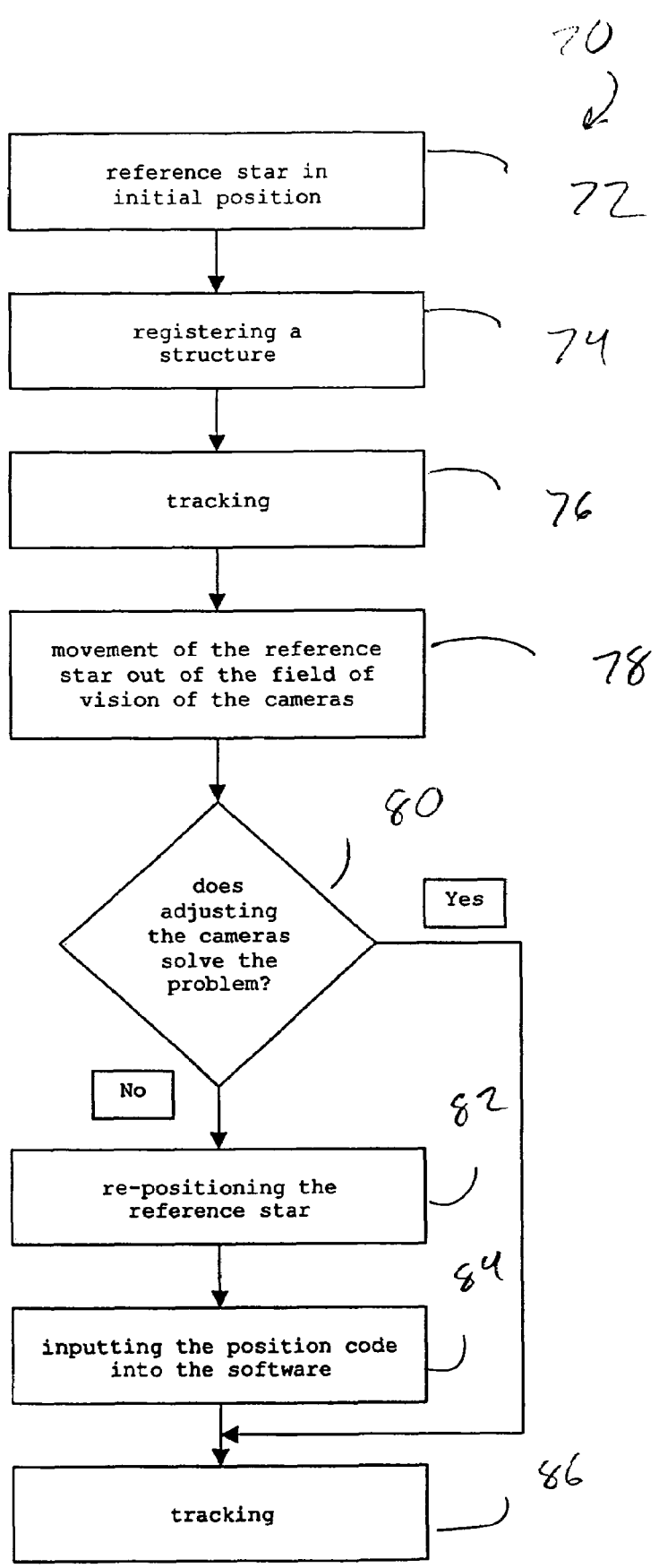
FIG. 6 is a flow diagram for re-calibrating a patient in accordance with an embodiment of the present invention.
Figure 7:
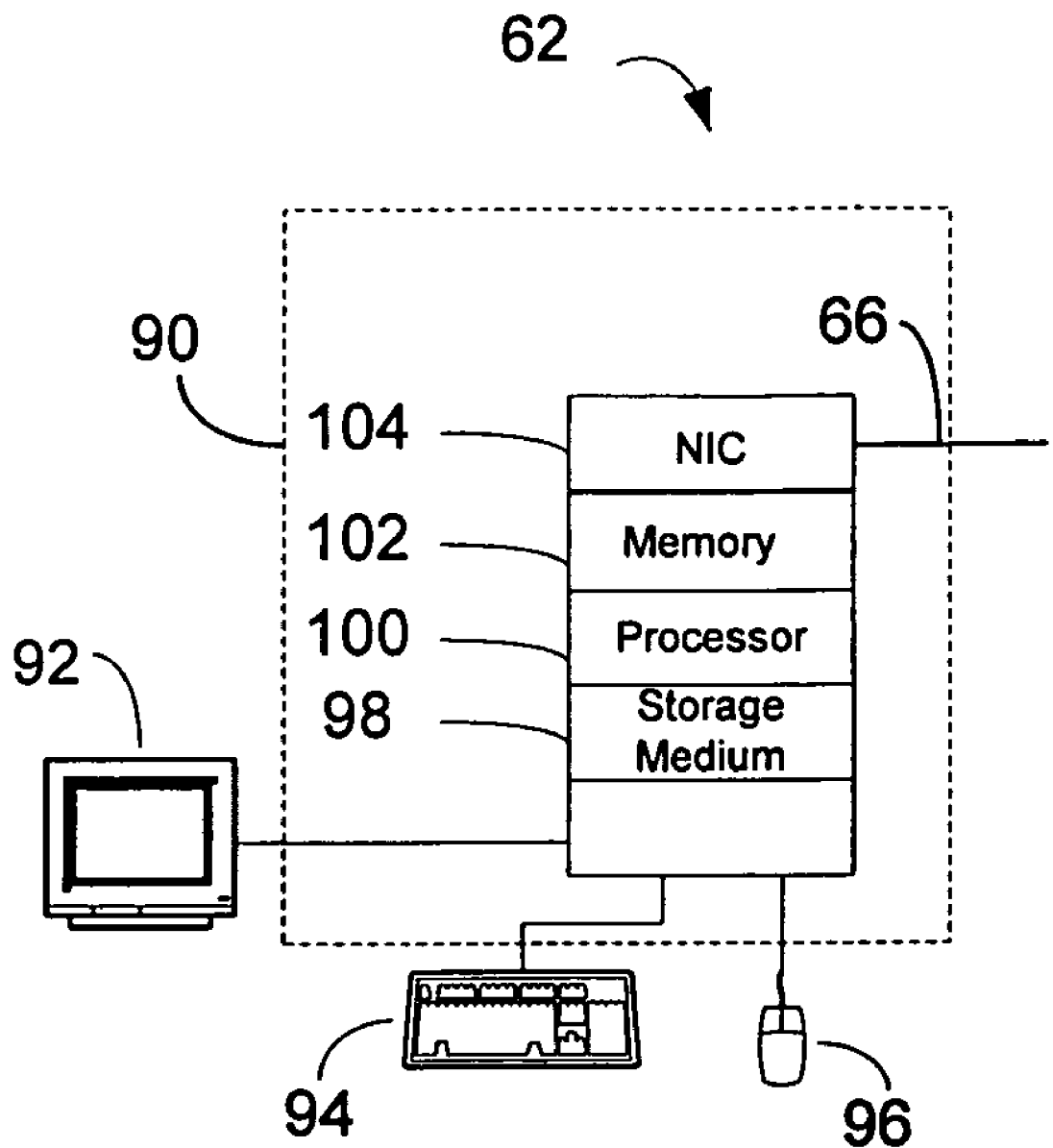
FIG. 7 is a block diagram of a computer system that can be used to implement the method of the present invention.

Moving now to FIG. 6, a flow diagram 70 illustrates an exemplary method of re-calibrating a body in a navigational system in accordance with an embodiment of the present invention. The flow diagram includes a number of process blocks arranged in a particular order. As should be appreciated, many alternatives and equivalents to the illustrated steps may exist and such alternatives and equivalents are intended to fall with the scope of the claims appended hereto. Alternatives may involve carrying out additional steps or actions not specifically recited and/or shown, carrying out steps or actions in a different order from that recited and/or shown, and/or omitting recited and/or shown steps. Alternatives also include carrying out steps or actions concurrently or with partial concurrence.

The flow diagram 70 of FIG. 6 illustrates the steps for registering and re-calibrating a body 2 after adjusting the position of a reference star connected to the body via an adapter 40 in accordance with the invention. In the initial position, the body, e.g., a particular body region or structure of a patient, is registered and the registered structure can be tracked. If the registered structure moves out of the field of vision 6 of the cameras 8, then an attempt can first be made to bring the reference star 4 back into the field of vision by adjusting the cameras 8. If this is unsuccessful, the reference star 4 is moved to a new position and a new position code, shown by way of example in FIGS. 5A and 5B, is communicated to the navigation system 60 or software. The new position code is used to calculate the new positional relationship of the reference star 4 with respect to the body 2 and the navigation system 60 continues to track the re-calibrated structure.

Beginning at step 72, a reference star adapter 40 in accordance with the present invention is coupled to a reference star 4 via a second fixing element 44. A first fixing element 42 of the reference star adapter 40 is coupled to a body 2 (e.g., patient body or instrument), and the second fixing element is placed in an initial position with respect to the first fixing element, such that the reference star is within the field of vision 6 of the cameras 8.

Next, at step 74 the reference star 4 is registered within the navigation system 60. Methods of registering a reference star in a navigation system are well known to those skilled in the art and will not be discussed in detail herein. Briefly, a number of points on the body 2 may be specified by the navigation system 60, and those points are identified using a calibrated instrument, such as a pointer (not shown) that includes reference markers. The reference markers on the instrument allow the navigation system 60, via the cameras 8, to track the instrument in three-dimensional space. The dimensions of the instrument are known by the navigation system and, therefore, based on the position of the markers attached to the instrument, the navigation system can ascertain the position in three-dimensional space of a distal end of the instrument. Touching points on the body 2 identified by the navigation system with the distal end of the instrument allows the navigation system to identify the location of the points in three-dimensional space with respect to the location of the reference star. The navigation system correlates the points identified on the body with preoperative images of the body 2. Since the reference star 4 is rigidly coupled to the body 2, the navigation system 60 can track the position of the body by tracking the position of the reference star, as identified in step 76.

Moving now to step 78, the reference star may move out of the field of vision 6 of the cameras 8. This can occur, for example, when the body 2 is rotated in a position that places the body 2 in front of the reference star 4 such that the body blocks the cameras' vision of the reference star 4. Alternatively, the rotation or movement of the body may place the reference star out of the field of vision 6 of the cameras 8. In either case, the navigation system cannot see the reference star and, therefore, cannot track the reference star 4 or the body 2.

In some instances, the reference star can be brought back into the field of view of the cameras by adjusting the position of the cameras. As indicated at step 80, if adjusting the cameras brings the reference star 4 back into the field of vision 6 of the cameras 8, then tracking of the reference star and body may proceed normally. If adjusting the camera position does not place the reference star into the field of vision of the cameras, then the geometric relationship of the reference star 4 with respect to the body 2 may be altered using the reference star adapter 40 of the present invention, as identified at step 82.

The reference star can be repositioned using the joint 46 of the reference star adapter 40. As was noted above, the joint 46 can include multiple joints to allow various degrees of movement. For example, the angle between the first fixing element 42 and the second fixing element 44 may be altered using the turning joint A. Additionally, the length of the second fixing element 44 can be increased or decreased using the bearing joint B. By manipulating the joint 46, the reference star 4 can be brought back into the field of vision 6 of the cameras 8. Once the reference star 4 is placed back into the field of vision of the cameras, the new position is communicated to the computational unit 62 of the navigation system 60. The computational unit 62, knowing the new position of the second fixing element 44 with respect to the first fixing element 42 (and therefore the new position of the reference star 4 with respect to the body 2), automatically re-calibrates the reference star to the body. The re-calibration is performed without reacquiring points on the body 2, as was done in the initial registration. Thus, the present invention eliminates the step of manually re-registering a body in a navigation system when the reference star is repositioned after the body has been registered.

Moving to FIG. 5A an exemplary computational unit 62 for executing a computer program in accordance with the present invention is illustrated. The computational unit 62 includes a computer 90 for processing data, and a display 92 for viewing system information. The technology used in the display is not critical and may be any type currently available, such as a flat panel liquid crystal display (LCD) or a cathode ray tube (CRT) display, or any display subsequently developed. A keyboard 94 and pointing device 96 may be used for data entry, data display, screen navigation, etc. The keyboard 94 and pointing device 96 may be separate from the computer 90 or they may be integral to it. A computer mouse or other device that points to or otherwise identifies a location, action, etc., e.g., by a point and click method or some other method, are examples of a pointing device. Alternatively, a touch screen (not shown) may be used in place of the keyboard 94 and pointing device 96. A touch screen is well known by those skilled in the art and will not be described in detail herein. Briefly, a touch screen implements a thin transparent membrane over the viewing area of the display 92. Touching the viewing area sends a signal to the computer 90 indicative of the location touched on the screen. The computer 90 may equate the signal in a manner equivalent to a pointing device and act accordingly. For example, an object on the display 92 may be designated in software as having a particular function (e.g., view a different screen). Touching the object may have the same effect as directing the pointing device 96 over the object and selecting the object with the pointing device, e.g., by clicking a mouse. Touch screens may be beneficial when the available space for a keyboard 94 and/or a pointing device 96 is limited.

Included in the computer 92 is a storage medium 98 for storing information, such as application data, screen information, programs, etc. The storage medium 98 may be a hard drive, for example. A processor 100, such as an AMD Athlon 64™ processor or an Intel Pentium IV® processor, combined with a memory 102 and the storage medium 98 execute programs to perform various functions, such as data entry, numerical calculations, screen display, system setup, etc. A network interface card (NIC) 104 allows the computer 90 to communicate with devices external to the computational unit 62.

The actual code for performing the functions described herein can be easily programmed by a person having ordinary skill in the art of computer programming in any of a number of conventional programming languages based on the disclosure herein. Consequently, further detail as to the particular code itself has been omitted for sake of brevity.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method of re-calibrating a previously registered body in a navigation system, said body being coupled via at least one joint to a plurality of reference markers that are detectable by the navigation system, and the navigation system having a specified field of vision in which the markers are detectable, said navigation system storing position data of the registered body, comprising the steps of:
   re-positioning the plurality of reference markers with respect to the body such that the plurality of reference markers are within the field of vision of the navigation system; and
   detecting a change in position of the reference markers with respect to the body.

2. The method of claim 1, further comprising the step of applying the change in position of the reference markers to the stored position data.

3. The method of claim 2, wherein the step of applying the change in position of the reference markers to the stored position data includes the step of applying the change in position of the reference markers to the stored position data after motion of the plurality of reference markers has not been detected for a preset time period.

4. The method of claim 2, wherein the step of applying the change in position of the reference markers to the stored position data includes the step of continuously applying the change in position of the reference markers to the stored position data.

5. The method of claim 2, wherein the step of re-positioning the plurality of reference markers includes the step of locking the plurality of reference markers in a known position.

6. The method of claim 1, wherein the step of detecting a change in position of the reference markers includes the step of reading position data from the joint.

7. The method of claim 6, further comprising the step of transmitting the position data to a computational unit.

8. The method of claim 7, wherein the step of transmitting the position data to the computational unit includes the step of wirelessly transmitting the position data to the computational unit.

9. The method of claim 1, wherein the step of re-positioning the plurality of reference markers includes the step of using an actuator to automatically change the position of the plurality of reference markers.

10. A computer program in a computer-readable medium which, when loaded onto a computer or running on a computer, performs the method as set forth in claim 1.

11. A program embodied in a computer-readable medium for re-calibrating a previously registered body in a navigation system, said body being coupled via at least one joint to a plurality of reference markers that are detectable by the navigation system, and the navigation system having a specified field of vision in which the markers are detectable, said navigation system storing position data of the registered body, comprising:
   code that provides an indication that the plurality of reference markers are not within the field of vision of the navigation system; and
   code that detects a change in position of the reference markers with respect to the body.

12. A system for re-calibrating a previously registered body in a navigation system, said body being coupled via at least one joint to a plurality of reference markers that are detectable by the navigation system, and the navigation system having a specified field of vision in which the markers are detectable, said navigation system storing position data of the registered body, comprising:
   a processor circuit having a processor and a memory;
   a calibrating system stored in the memory and executable by the processor, the calibrating system comprising:
   logic that generates an indication that the plurality of reference markers are not within the field of vision of the navigation system; and
   logic that detects a change in position of the reference markers with respect to the body.

* * * * *